US010285733B2

(12) United States Patent
De Oto et al.

(10) Patent No.: US 10,285,733 B2
(45) Date of Patent: May 14, 2019

(54) DEVICE FOR EXTERNAL ORTHOPEDIC FIXATIONS

(71) Applicants: AUTOMOBILI LAMBORGHINI S.P.A., Sant'Agata Bolognese (BO) (IT); AZIENDA OSPEDALIERO-UNIVERSITARIA DI BOLOGNA POLICLINICO S. ORSOLA—MALPIGHI, Bologna (BO) (IT); ISTITUTO ORTOPEDICO RIZZOLI, Bologna (BO) (IT)

(72) Inventors: Luciano De Oto, Crevalcore (IT); Marco De Luca, Ravenna (IT); Mauro Girolami, Bologna (IT); Stefano Boriani, Bologna (IT); Maria Concetta Nucci, Vasto (IT)

(73) Assignees: AUTOMOBILI LAMBORGHINI S.P.A., Sant'Agata Bolognese (BO) (IT); ISTITUTO ORTOPEDICO RIZZOLI, Bologna (BO) (IT); AZIENDA OSPEDALIERO-UNIVERSITARIA DI BOLOGNA POLICLINICO S. ORSOLA-MALPIGHI, Bologna (BO) (IT)

( * ) Notice: Subject to any disclaimer, the term of this patent is extended or adjusted under 35 U.S.C. 154(b) by 24 days.

(21) Appl. No.: 15/329,317

(22) PCT Filed: Jul. 31, 2015

(86) PCT No.: PCT/IB2015/055819
§ 371 (c)(1),
(2) Date: Jan. 26, 2017

(87) PCT Pub. No.: WO2016/024184
PCT Pub. Date: Feb. 18, 2016

(65) Prior Publication Data
US 2017/0215922 A1 Aug. 3, 2017

(30) Foreign Application Priority Data

Aug. 14, 2014 (IT) .............................. MI2014A1499

(51) Int. Cl.
*A61B 17/62* (2006.01)
*A61B 17/64* (2006.01)

(52) U.S. Cl.
CPC ............ *A61B 17/62* (2013.01); *A61B 17/645* (2013.01); *A61B 17/6441* (2013.01)

(58) Field of Classification Search
CPC .... A61B 17/62; A61B 17/6441; A61B 17/645
(Continued)

(56) References Cited

U.S. PATENT DOCUMENTS 2,055,024 A * 9/1936 Bittner, Jr. ............. A61B 17/62
606/56
5,372,597 A * 12/1994 Hotchkiss .......... A61B 17/6425
602/20

(Continued)

FOREIGN PATENT DOCUMENTS

DE 4013822 A1 10/1991

OTHER PUBLICATIONS

International Search Report and Written Opinion for International Application No. PCT/IB2015/055819. (10 Pages) (dated Nov. 18, 2015).

*Primary Examiner* — Pedro Philogene
*Assistant Examiner* — David C Comstock
(74) *Attorney, Agent, or Firm* — Lucas & Mercanti, LLP

(57) ABSTRACT

A device for external orthopedic fixations, which has one or more frames which have a substantially and/or partially annular shape and are suitable for being arranged around a limb to surround it at least partially, wherein one or more rods are fixed to a frame by means of a locking mechanism is provided. The device has two jaws which, when closed, (Continued)

tighten the locking mechanism to a portion of the frame by exerting a prevalently axial force, wherein the jaws are closed by means of a cam mechanism suitable for being actuated by rotating a lever pivoted to a first jaw and provided with one or more cam surfaces cooperating with a surface of the second jaw.

26 Claims, 9 Drawing Sheets

(58) Field of Classification Search
USPC .................................. 606/56, 54, 57, 58, 59
See application file for complete search history.

(56) References Cited

U.S. PATENT DOCUMENTS

| | | | |
|---|---|---|---|
| 5,888,197 A | 3/1999 | Mulac et al. | |
| 2002/0172549 A1* | 11/2002 | Koros | F16M 13/022 403/322.4 |
| 2002/0177754 A1* | 11/2002 | Phillips | A61B 17/02 600/234 |
| 2007/0049930 A1* | 3/2007 | Hearn | A61B 17/62 606/56 |
| 2009/0264882 A1* | 10/2009 | Steiner | A61B 17/62 606/56 |
| 2012/0203225 A1 | 8/2012 | Mingozzi et al. | |
| 2013/0018374 A1 | 1/2013 | Edelhauser et al. | |
| 2015/0305776 A1* | 10/2015 | Ross | A61B 17/60 606/56 |
| 2016/0199098 A1* | 7/2016 | Slagle | A61B 17/6458 606/59 |
| 2017/0181800 A1* | 6/2017 | Nikonovas | A61B 34/10 |
| 2017/0224383 A1* | 8/2017 | Wong | A61B 17/6458 |

\* cited by examiner

DEVICE FOR EXTERNAL ORTHOPEDIC FIXATIONS

CROSS-REFERENCE TO RELATED APPLICATIONS

This application is a 371 of PCT/IB2015/055819, filed Jul. 31, 2015, which claims the benefit of Italian Patent Application No. MI2014A001499, filed Aug. 14, 2014.

FIELD OF THE INVENTION

The present invention relates to a device for external orthopedic fixations, in particular a device of the type also known as Ilizarov apparatus.

BACKGROUND OF THE INVENTION

US 2012/203225 A1 and U.S. Pat. No. 5,888,197 describe devices for orthopedic fixations comprising two or more frames which can be arranged next to a limb and are connected by a rod fixed to the frames by means of a locking mechanism comprising two jaws which can be closed by a cam mechanism provided with a lever to tighten a locking mechanism to a portion of the frame. The frames of these known devices, being formed by straight bars, cannot be arranged around a limb, in particular to arrange wires, bars or nails in a radial configuration with respect to this limb, as it is instead necessary in the Ilizarov apparatuses. The jaws also exert a force perpendicular to the axis of the frame to which are tightened, then a force which is not prevalently axial.

US 2013/0018374 A1 describes a device for orthopedic fixations comprising two frames of annular shape that can be arranged around a limb and are connected by a plurality of rods fixed to the frames by means of locking mechanisms comprising two jaws which can be closed by a cam mechanism provided with a lever. These jaws do not tighten the frames but bring near two pins which are inserted in corresponding longitudinal holes formed in the frames to prevent the sliding of a locking mechanism around a frame, otherwise possible through a screw kinematic mechanism.

This known device has a relatively complex structure which makes the device expensive and complex to use. In addition, the operation of this known device requires the presence of many metal parts that make the same device heavy and opaque to X-rays, so as to adversely interfere during radiological examinations. Moreover, the rods may be fixed only in a limited number of positions corresponding to the number of holes formed in the frames, so as to prevent a precise application of wires, bars or nails in a radial configuration with respect to the limb, as is instead required in the Ilizarov apparatuses.

DE 40 13 822 A1 describes a device for orthopedic fixations comprising two frames of annular shape that can be arranged around a limb and are interconnected by a plurality of rods fixed to the frames by means of a screw locking mechanisms that apply an axial force on a frame but also make difficult its use in a medical field because of the opacity to X-rays of the screws and of the relative complexity and slowness of their tightening in critical situations.

SUMMARY OF THE INVENTION

The object of the present invention is therefore to provide a device free from said drawbacks. Said object is achieved with a device whose main features are specified in the first claim, while other features are specified in the remaining claims.

Thanks to the particular structure of the rods, of the frames and of the locking mechanisms, the device according to the present invention is relatively light and easy to use, and can be integrally or nearly integrally made of a material transparent to X-rays, in particular of a composite material.

Also, the locking mechanisms tighten the rods to the frame with a quick and precise cam mechanism, so as to speed up and simplify the procedures for installation or removal of the device around the limb, which procedures are generally critical both for the patient and the doctors assisting him.

The locking mechanisms are also provided with special seats which prevent or limit the movements of the rods with respect to these mechanisms when the jaws are tightened to the frame, so as to provide a dual locking or unlocking function by operating a single lever.

The frames preferably comprise more portions which can be joined together in a simple and fast manner and which can be provided with radial holes which allow the direct assembly of mechanical devices and/or wires in tension and/or be equipped with arched grooves and ribs to limit the relative positions of the locking mechanisms with respect to the frames. Thanks to the particular shape of the ends of the frames portions, the locking mechanisms may be fixed at any point of the frame, also at these ends.

The rods which are connected to the frame by means of the locking mechanisms may be provided with special clamps or housings that allow to orient and maintain in specific positions with respect to the rods themselves the elongated members which connect the limb to the present device. In particular, the housing of a rod can contain a cable clamp and be provided with a slot, so as to simplify and speed up the procedure in which a wire suitable to connect the limb to the present device is fixed to the rod.

BRIEF DESCRIPTION OF THE DRAWINGS

Further advantages and characteristics of the device according to the present invention will become apparent to those skilled in the art from the following detailed and non-limiting description of some embodiments thereof with reference to the accompanying drawings in which.

DETAILED DESCRIPTION OF THE INVENTION

Figure 1:
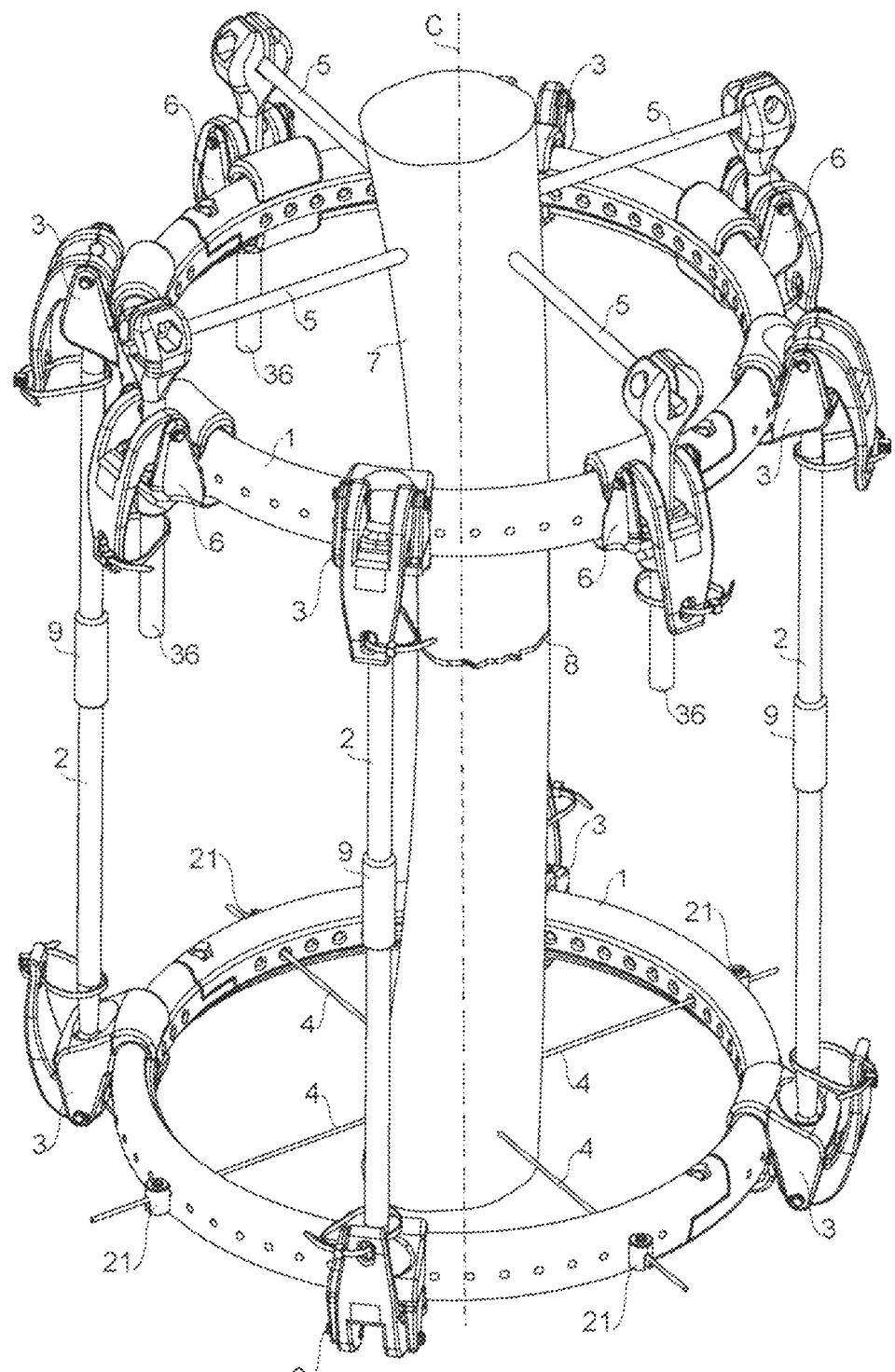
FIG. 1 shows a perspective view of a first embodiment of the device.

Referring to FIG. 1, it is seen that the present device comprises in a known way one or more frames, in particular two frames 1 of a substantially and/or partially annular shape, which are adapted to be placed around a limb, for example of a person or an animal, for at least partially surrounding this limb. One or more first rods, in particular four first rods 2 (a first rod is hidden in FIG. 1), connect the two frames 1 and can be fixed in a removable manner to at least a frame 1 by means of at least one first locking mechanism 3. One or more elongated members, for example wires 4, bars or nails 5, can be fixed in removable manner to at least one frame 1, directly, such as wires 4 in the figure, or by at least one second locking mechanism 6, such as for example nails 5. These elongated members 4, 5 are adapted to penetrate into at least one bone 7 in the limb provided with the present device, for example for fixing two portions of bone 7 which are separated by a fracture 8. Rods 2 may be lengthened or shortened, for example by rotating axially at least one threaded bush 9 in which threaded ends of two portions of a rod 2 are screwed.

Figure 2:
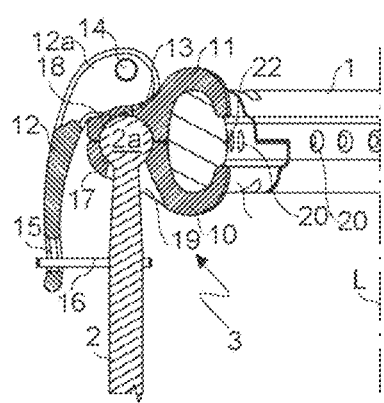
FIG. 2 shows an enlarged view in longitudinal section of a first locking mechanism of the device of FIG. 1.
Figure 3:
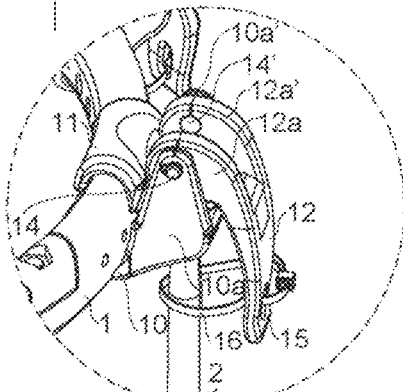
FIG. 3 shows an enlarged perspective view of the locking mechanism of FIG. 2.

Referring now also to FIGS. 2 and 3, it is seen that the first locking mechanism 3 comprises at least two jaws 10, 11 which, when closed, tighten the locking mechanism 3 to a portion of the frame 1. When they are closed and tighten the portion of frame 1, jaws 10, 11 exert a force prevalently axial, namely along a longitudinal axis L of frame 1, in particular an axis substantially parallel to the central axis C of frame 1. To tighten the portion of frame 1, jaws 10, 11 can be closed by means of a cam mechanism operated by rotating at least one lever 12. In particular, lever 12 can be pivoted to a first jaw 10 and be provided with one or more cam surfaces, in particular two cam surfaces 13 (one of these surfaces is shown with a dashed line in FIG. 2) cooperating with at least one surface of the second jaw 11. Lever 12 can be pivoted to the first jaw 10 by means of one or more pins, in particular two pins 14, 14' aligned to each other and inserted in holes formed in two walls 10a, having for example a substantially triangular profile, which extend from the first jaw 10, and in two walls 12a, 12a', having for example a substantially elliptical profile, which extend from lever 12 and comprise a cam surface 13. The free end of lever 12 may be provided with an opening 15 for tying lever 12 to a rod 2 with a clamp 16, so as to prevent the accidental rotation of lever 12 and therefore the opening of jaws 10, 11. The locking mechanism 3 may comprise one or more seats 17, 18 for a rod 2. Seats 17, 18 are preferably arranged between the two walls 10a which extend from the first jaw 10. Seats 17, 18 have a shape substantially complementary to the shape of a portion 2a of rod 2. In the present embodiment, the portion 2a of rod 2 is substantially spherical and/or is arranged at one end of rod 2 and/or seats 17, 18 have a concave shape adapted to receive a sphere portion having substantially same diameter of portion 2a of rod 2. When jaws 10, 11 are closed and tightened on frame 1, seats 17, 18 tighten portion 2a of rod 2, thus preventing a relative movement of rod 2 with respect to at least one axis of the locking mechanism 3 and then of frame 1. Seat 17 of the first jaw 10 is connected with the outside through at least one opening 19 having a substantially frustoconical shape, in particular having an apex angle less than 80° and/or greater than 30°.

The cross-section of a portion of frame 1 may be substantially elliptical, with the major axis of the ellipse substantially parallel to the longitudinal axis L. Frame 1 can also be provided with one or more radial holes, in particular a series of radial holes 20 spaced with a pitch comprised between 3° and 10°. One or more mechanical devices can be inserted in the radial holes 20. In particular, one or more wires 4 can be stretched between two holes 20 and locked by two cable clamps 21, in particular having a substantially cylindrical shape with the central axis substantially parallel to the longitudinal axis L of frame 1. The inner end of the radial holes 20 is preferably countersunk, so that a wire 4 can be stretched without abrupt angles between two holes which are not aligned along a diameter of frame 1. The internal profile of jaws 10, 11 has a concave profile substantially complementary to the external profile of a portion of frame 1, for example a profile substantially as an arc of ellipse. Frame 1 also has one or more protuberances or recesses, such as a circular or partially circular rib 22 arranged along the inner edge of frame 1 and/or between the free ends of jaws 10, 11, so as to guide and arrange the latter in a defined position when they are closed and tightened on frame 1.

Figure 4:
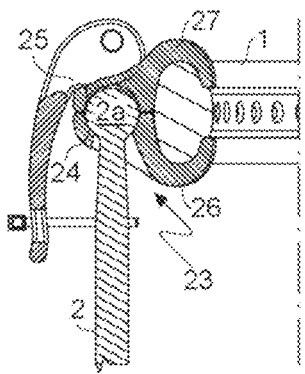
FIG. 4 shows a second embodiment of the locking mechanism of FIG. 2.

Referring to FIG. 4, it is seen that the first locking mechanism 23 according to a second embodiment is substantially equal to the first locking mechanism 3, with the difference that seats 24 and 25 are slightly bigger than portion 2a of rod 2, in particular they together form a substantially spherical seat having a diameter greater than the diameter of portion 2a of rod 2, so that portion 2a of rod 2 can rotate around one or more axes, in particular around three axes, in seats 24 and 25.

In general, in the blocking mechanisms according to the present invention the seats for the rods may be shaped so that when the jaws are closed and tightened on the frame a rod can rotate around one, two or three axes, for example around the central axis of the rod and/or around a radial axis of the frame and/or around an axis tangential to the frame, and/or translate along an axis with respect to the locking mechanism.

Figure 5:
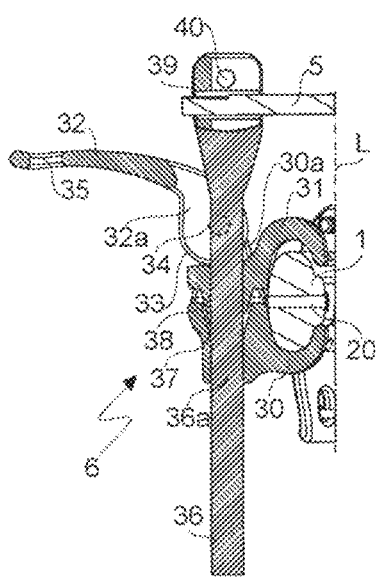
FIG. 5 shows an enlarged view in longitudinal section of a second locking mechanism of the device of FIG. 1 in an unlocked position.
Figure 6:
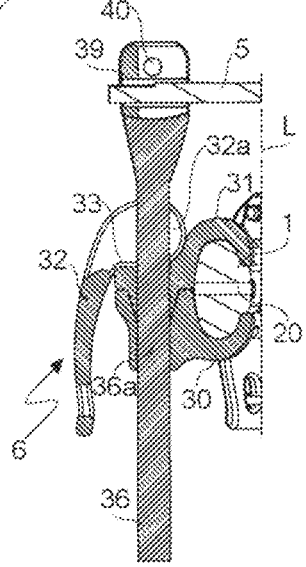
FIG. 6 shows the locking mechanism of FIG. 5 in a locked position.

Referring to FIGS. 5 and 6, it is seen that the second locking mechanism 6 is similar to the first locking mechanism 3 since it also comprises at least two jaws 30, 31 adapted to be closed to tighten the locking mechanism 6 to a portion of frame 1 by exerting a force prevalently axial, namely substantially parallel to the longitudinal axis L of frame 1. To tighten the portion of frame 1, jaws 30, 31 are adapted to be moved towards each other by at least one lever 32 which can be pivoted to a first jaw 30 and be provided with one or more cam surfaces, in particular two cam surfaces 33 cooperating with at least one surface of the second jaw 31. Lever 32 can be pivoted to the first jaw 30 by means of one or more pins, in particular two pins 34 aligned with each other and inserted in holes formed in two walls 30*a*, having for example a substantially triangular profile, which extend from the first jaw 30, and two walls 32*a*, having for example a substantially elliptical profile, which extend from lever 32 and which comprise a cam surface 33. The free end of lever 32 may be provided with an opening 35 for tying lever 32 to a rod 36 with a clamp, so as to prevent the accidental rotation of lever 32 and therefore the opening of jaws 30, 31. The locking mechanism 6 may include one or more seats 37, 38 for rod 36. Seats 37, 38 have a shape substantially complementary to the shape of a portion 36*a* of rod 36. In the present embodiment, portion 36*a* of rod 36 is substantially cylindrical and seats 37, 38 have a concave shape, in particular substantially cylindrical, adapted to receive a portion of a cylinder having substantially the same diameter of portion 36*a* of rod 36. In particular, seat 38 of jaw 31 has externally a substantially frustoconical shape, which is provided with longitudinal slots (not visible in the figures) and which is complementary to a cavity, also for example with a substantially frustoconical shape, of seat 37 of jaw 30 for rod 36. When jaws 30, 31 are tightened on frame 1, seats 37, 38 are coupled, seat 38 of jaw 31 is deformed internally through the longitudinal slots and it tighten portion 36*a* of rod 36, thus preventing a sliding along its axis and/or a rotation around this axis of rod 36 relative to the second locking mechanism 6 and thus relative to frame 1. Rod 36 may in turn be provided with a clamp 39, in particular made in one piece with rod 36, to mechanically connect, in particular by tightening it with a screw 40, a nail 5 to frame 1 through the second locking mechanism 6. Clamp 39 is preferably arranged at one end of rod 36 and preferably comprises a mobile part so that nail 5 can form with the central axis of rod 36 at an angle comprised between 60° and 120°.

Figure 7:
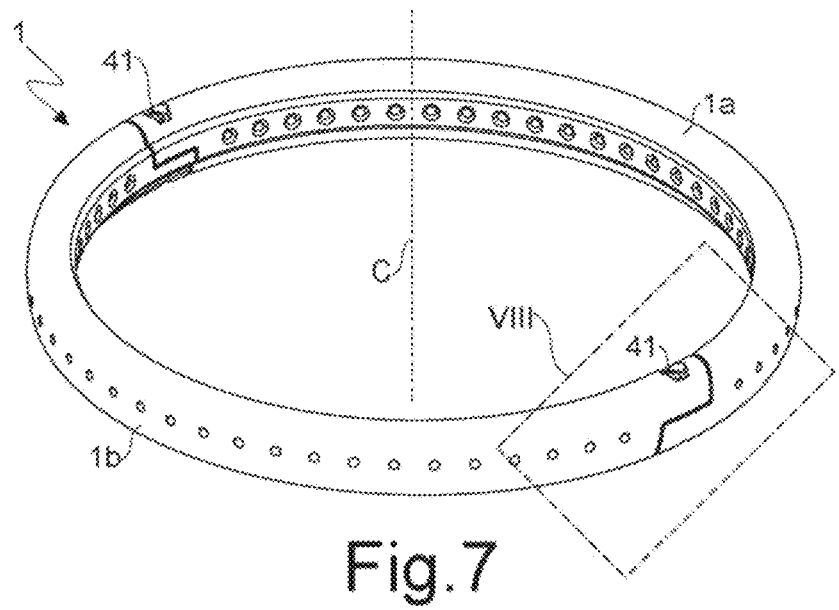
FIG. 7 shows a perspective view of a frame of the device of FIG. 1.
Figure 8:
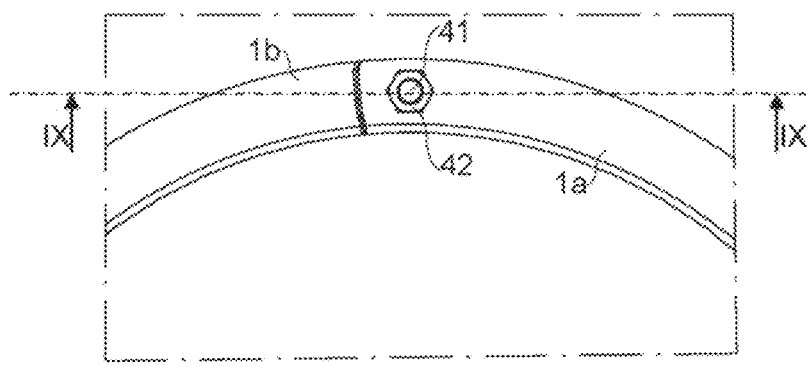
FIG. 8 shows detail VIII of FIG. 7.
Figure 9:
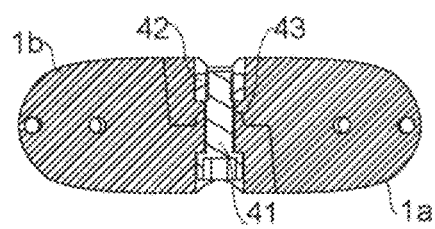
FIG. 9 shows section IX-IX of FIG. 8.

Referring to FIGS. 7 to 9, it is seen that frame 1 may have a substantially annular shape and/or comprise more frame portions connected to each other, in particular two frame portions 1*a*, 1*b* having a half-ring shape. Portions 1*a*, 1*b* of frame 1 can be joined together by means of a screw 41 inserted respectively in two holes that are formed at one end of portions 1*a*, 1*b*, are aligned with each other and are substantially parallel to the central axis C of frame 1. The adjacent ends of portions 1*a*, 1*b* are shaped with complementary profiles so as to achieve a form coupling in the region in which screw 41 passes through these holes. With this arrangement, these ends can be locked to each other, so that portions 1*a*, 1*b* form frame 1 by screwing screw 41 into a nut 42. The ends of portions 1*a*, 1*b* are arranged between the head of screw 41, housed in a seat formed in portion 1*b*, and nut 42, housed in a seat formed in portion 1*a*, so that neither screw 41 nor nut 42 protrude from frame 1. With this arrangement a locking mechanism can be fixed to frame 1 also at screw 41. Furthermore, in particular around the hole for screw 41, the end of portion 1*a* of frame 1 is provided with at least one protrusion or recess 43 which realizes a form coupling with a corresponding recess or protrusion formed at the contiguous end of portion 1*b* of frame 1.

Figure 10:
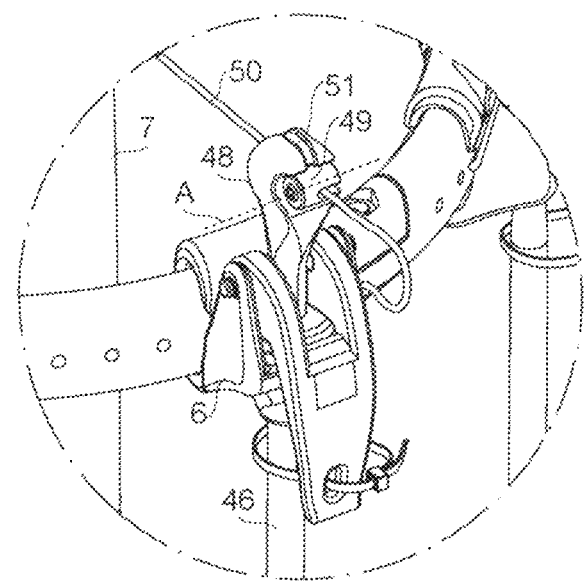
FIG. 10 shows an enlarged perspective view of the locking mechanism of FIG. 5 with a rod according to another embodiment.

Referring to FIG. 10, it is seen that the locking mechanism 6 can be connected to a rod 46 according to an embodiment provided with a housing 48 for a cable clamp 49 adapted to stretch a wire 50 between limb 7 and rod 46. The cable clamp 49 may have a substantially cylindrical shape, so that it can rotate in housing 48 around an axis A substantially perpendicular to the stretched wire 50. Housing 48 is also preferably provided with a slot 51 so that wire 50 can form with rod 45 an angle comprised between 60° and 120° when the cable clamp 49 rotates in housing 48. In addition, thanks to slot 51, wire 50 already provided with the cable clamp 49 can be fixed to rod 46. Housing 48 is preferably made in one piece with rod 46.

Figure 11:
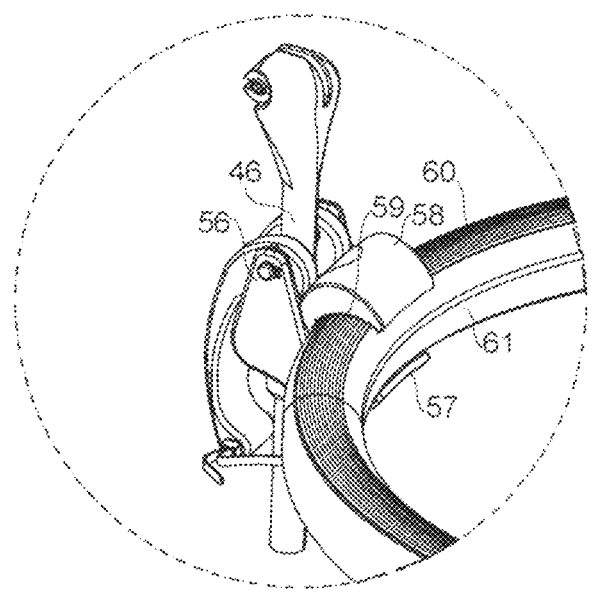
FIG. 11 shows an enlarged perspective view of a second embodiment of the locking mechanism of FIG. 5 and of a second embodiment of the frame of FIG. 7.

Referring to FIG. 11, it is seen that the second locking mechanism 56 according to a second embodiment is substantially equal to the first embodiment, as well as similar to the first locking mechanism 3, however it comprises two jaws 57, 58 having inner surfaces provided with ribs or grooves 59 which carry out a form coupling with corresponding grooves or ribs 60 arranged along arcs of circumference of a frame 61 according to a second embodiment. Jaws 57, 58 are sufficiently wide to allow the tightening of the locking mechanism 56 on frame 61 at a plurality of positions defined by the possible form couplings between ribs or grooves 59, 60. In this way, a rod 46 can be fixed to frame 61 by means of the second locking mechanism 56 with an orientation parallel to the central axis of frame 61 or inclined with respect to the latter with a given angle which is comprised between 0° and 30°, for example in steps of 5°, and which it is defined by the relative position of the ribs or grooves 59, 60.

Figure 12:
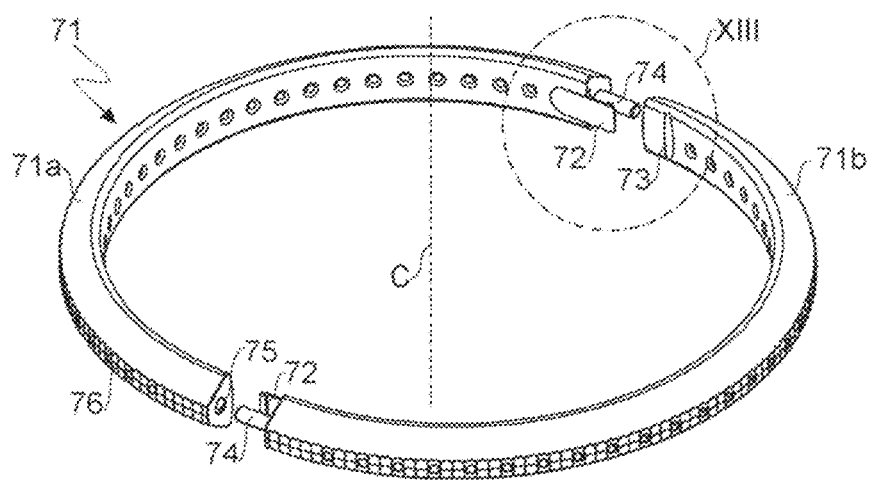
FIG. 12 shows a third embodiment of the frame of FIG. 7.
Figure 13:
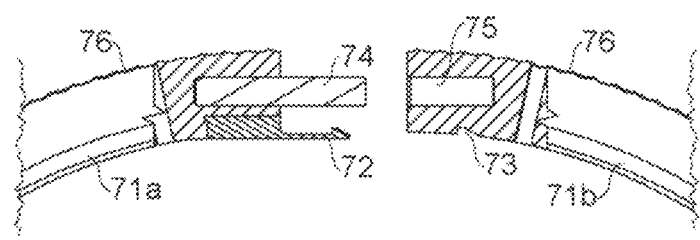
FIG. 13 shows detail XIII of FIG. 12 enlarged and partially sectioned.
Figure 14:
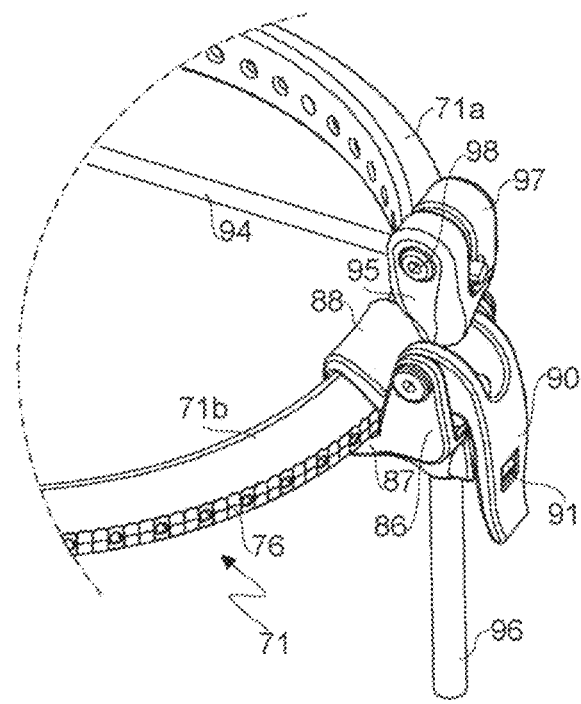
FIG. 14 shows a perspective view of a third embodiment of the locking mechanism of FIG. 5.
Figure 15:
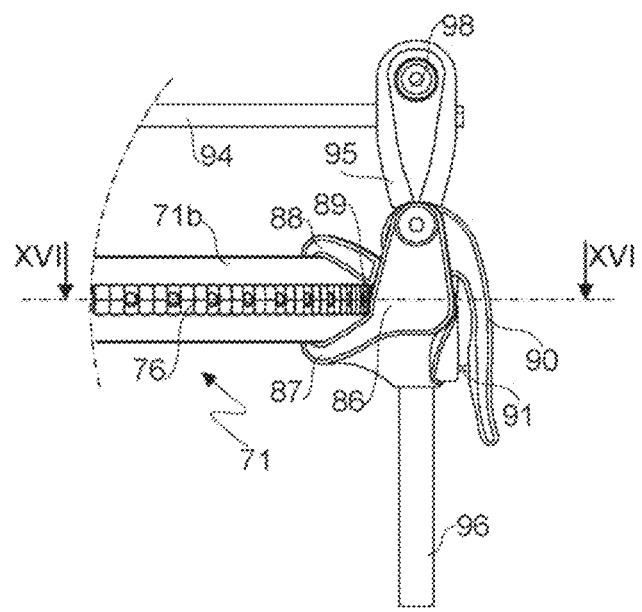
FIG. 15 shows a side view of the locking mechanism of FIG. 14.
Figure 16:
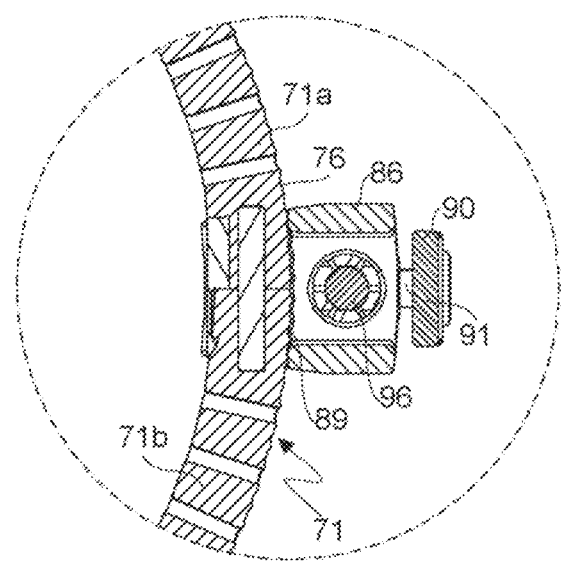
FIG. 16 shows section XVI-XVI of FIG. 15.
Figure 17:
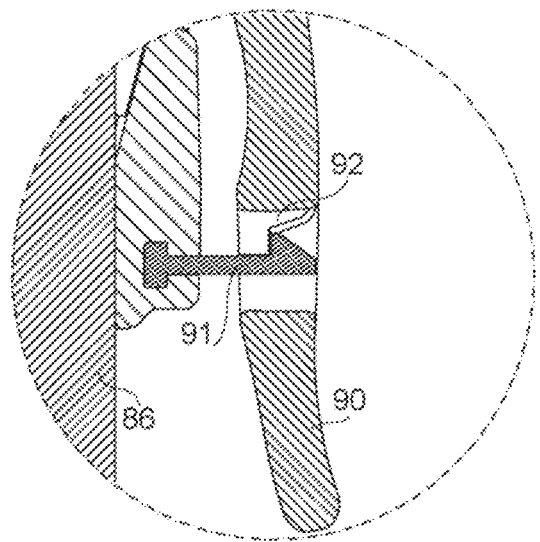
FIG. 17 shows an enlarged and partial longitudinal section of the locking mechanism of FIG. 14.

Referring to FIGS. 12 and 13, it is seen that frame 71 according to a third embodiment, similar to the first embodiment, is formed by two or more portions 71*a* and 71*b* having one end provided with a flexible hook 72 adapted to be snap-fitted into a corresponding cavity 73 formed at one end of the adjacent portion 71*b* or 71*a* of frame 71. The ends of portions 71*a* and 71*b* of frame 71 may also be provided with a pin 74 adapted to be inserted into a corresponding hole 75 formed at one end of the adjacent portion 71*b* or 71*a*. Pin 74 is arranged along an axis substantially parallel to an axis tangent to frame 71. The flexible hook 72 and/or cavity 73 are arranged along the inner wall of frame 71. The cross-section of frame 71 has a substantially trapezoidal shape, with the major base facing the center of frame 71 and the minor base toward the outside. The major base is slightly convex towards the center of frame 71 and/or the minor base, namely the outer wall of frame 71, can be provided with grooves or ribs 76, in particular grooves with the shape of a cylindrical portion substantially parallel to the central axis C of frame 71. Grooves 76 can act as seats for mechanical devices, in particular cable clamps (not shown in the figure) with a substantially cylindrical shape that stretch wires inserted in the radial holes of frame 71. For this reason, the radial holes of frame 71 are arranged substantially at the center of grooves 76. The pitch between the grooves or ribs 76 may be comprised between 1° and 3°.

Referring to FIGS. 14 to 17, it is seen that the second locking mechanism 86 according to a third embodiment is substantially equal to the first two embodiments, as well as similar to the first locking mechanism 3, however it comprises at least two jaws 87, 88 which have a curved profile, for example hook-shaped, complementary with the outer profile of frame 71 according to the third embodiment. A portion of the second locking mechanism 86, in particular arranged between the two jaws 87, 88, is provided with ribs or grooves 89 which carry out a form coupling with the grooves or ribs 76 arranged along frame 71. In this way, the second locking mechanism 86 can be arranged at given positions along frame 71. To tighten the portion of frame 71, jaws 87, 88 are closed, so as to be moved one towards the other, by at least one lever 90 through a cam mechanism as in the blocking mechanisms according to the other embodiments. The second locking mechanism 86 is also provided with at least one flexible hook 91 adapted to engage in a seat 92 formed in lever 90, so as to prevent an accidental opening of jaws 87, 88. The flexible hook 91 can be bent, for example, with the tip of a screwdriver, to unlock lever 90. The second locking mechanism 86 connects a nail 94 to frame 71 by means of a clamp 95 that can be made in one piece with a rod 96 and/or is provided with a moving part 97 that can tighten nail 94 on clamp 95 by screwing a screw 98.

Figure 18:
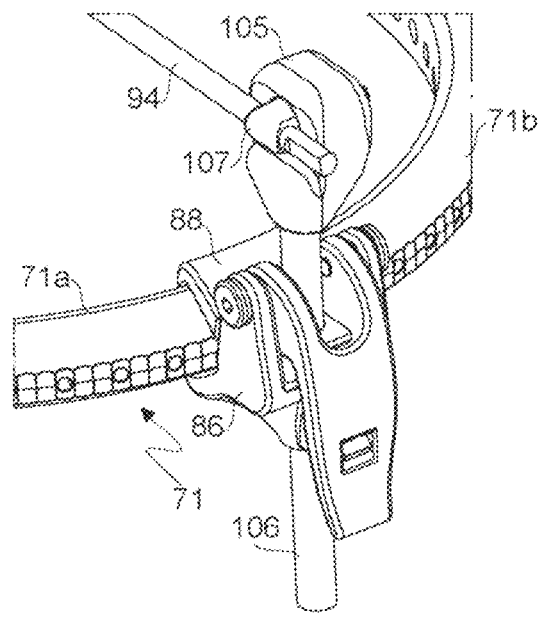
FIG. 18 shows a perspective view of the locking mechanism of FIG. 14 with a rod according to a further embodiment.
Figure 19:
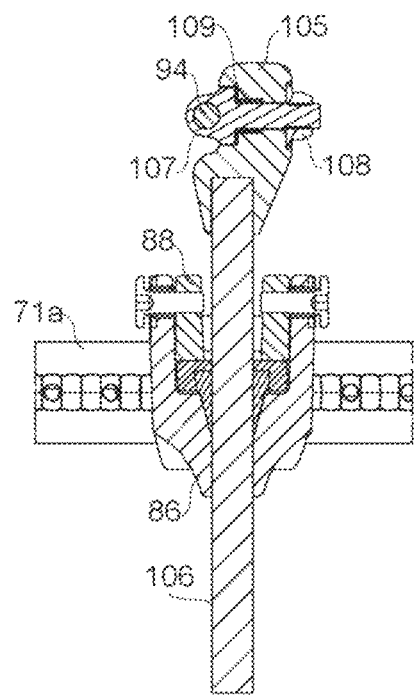
FIG. 19 shows a partial and enlarged longitudinal section of the locking mechanism of FIG. 18.

Referring to FIGS. 18 and 19, it is seen that the second locking mechanism 86 can also connect wire 50 to frame 71 by means of clamp 105 joined to rod 106. Clamp 105 is provided with a movable part 107 which can tighten nail 94 against clamp 105. The movable part 107 comprises in particular a pin inserted in a hole made in clamp 105 along an axis substantially perpendicular to rod 106 and/or to nail 94. An end of pin 107 is provided with a head comprising a hole in which nail 94 can slide, while the other end is threaded, so that a nut 108 can be screwed around pin 107, thus tightening clamp 105 between nut 108 and nail 94, so that nail 94, urged against one side of clamp 105, cannot slide in the hole of pin 107 and prevents the rotation of pin 107 in clamp 105. A helical spring 109 is arranged around pin 107 in the hole of clamp 105 to remove nail 94 from clamp 105 when nut 108 is loosened. Nail 94 may be fixed to rod 106 by forming with the central axis of the latter an angle comprised between 60° and 120° according to the rotation of pin 107 in clamp 105.

Figure 20:
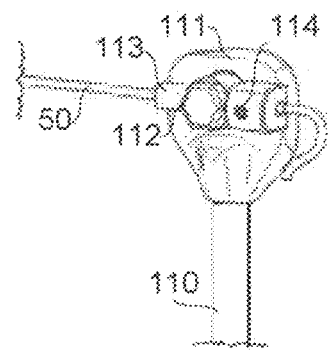
FIG. 20 shows a perspective view of a rod according to a further embodiment.
Figure 21:
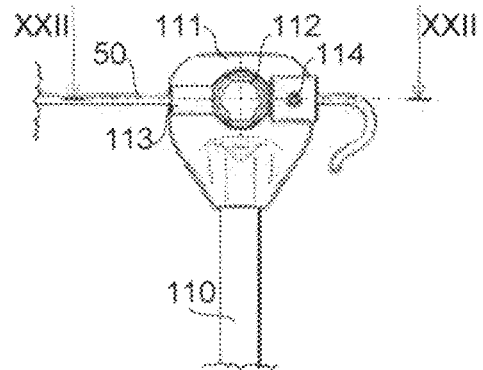
FIG. 21 shows a front view of the rod of FIG. 20.
Figure 22:
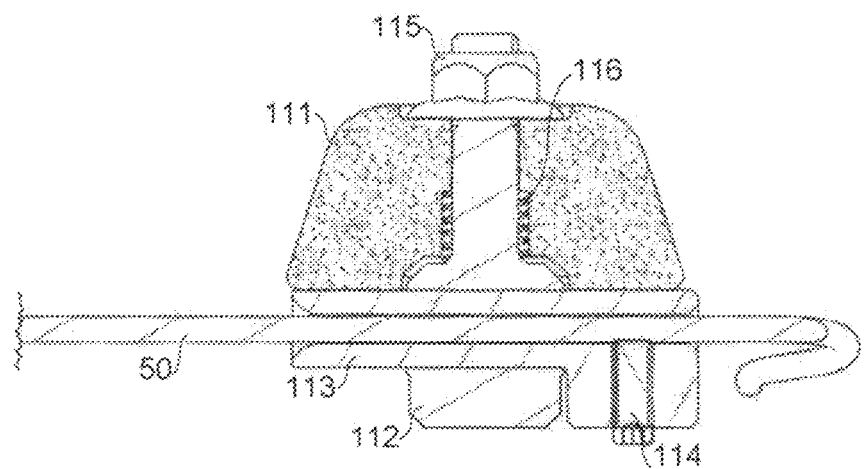
FIG. 22 shows section XXII-XXII of FIG. 21, enlarged.

Referring to FIGS. 20 to 22, it is seen that in a further embodiment rod 110 may be provided with a clamp 111 for wire 50. Clamp 111 is provided with a movable part 112 which can tighten a cable clamp 113 in which wire 50 can slide or be blocked by a screw 114 that can urge perpendicularly to wire 50. The movable part 112 comprises in particular a pin inserted in a hole made in clamp 111 along an axis substantially perpendicular to rod 110 and/or to wire 50. One end of pin 112 is provided with a head comprising a housing in which the cable clamp 113 can slide, while the other end is threaded, so that a nut 115 may be screwed around pin 112, thereby tightening clamp 111 between nut 115 and the cable clamp 113, so that the latter, being urged against one side of clamp 111, cannot slide in the housing of pin 112 and prevents the rotation of pin 112 in clamp 111. A helical spring 116 is arranged around pin 112 in the hole of clamp 111 to remove the cable clamp 113 from clamp 111 when nut 115 is loosened. Wire 50 can be fixed to rod 110 by forming with the central axis of the latter an angle comprised between 60° and 120° according to the rotation of pin 112 in clamp 111.

Frames 1, 61 and/or 71, rods 2, 36, 46, 96, 106 and/or 111 and/or the locking mechanisms 3, 6, 23, 56 and/or 86 are preferably made of a composite material, in particular containing carbon fibers, more in particular short carbon fibers (length of between 5 and 200 mm, in particular between 20 and 30 mm), preferably through the manufacturing method described in patent application WO 2013/128312, which is included in its entirety by reference into the present application.

Other embodiments of the first and/or second locking mechanism may include technical features of the first and/or second locking mechanism according to all embodiments described and illustrated here.

Further variants and/or additions may be made by those skilled in the art to the embodiments here described and illustrated remaining within the scope of the following claims. In particular, further embodiments of the invention may comprise the technical features of one of the following claims with the addition of one or more technical features, taken singularly or in any mutual combination, described in the text and/or illustrated in the drawings.

The invention claimed is:

1. A device for external orthopedic fixations, which comprises one or more frames which have a substantially or partially annular shape and are suitable for being arranged around a limb to surround it at least partially,
   wherein one or more rods are fixed to a frame of said one or more frames by means of a locking mechanism provided with at least two jaws which, when closed, tighten the locking mechanism to a portion of the frame by exerting a prevalently axial force,
   wherein said jaws are closed by means of a cam mechanism suitable for being actuated by rotating a lever pivotable relative to a first jaw of the at least two jaws and provided with one or more cam surfaces cooperating with a surface of the second jaw of the at least two jaws,
   wherein said at least two jaws of the locking mechanism each comprise one or more seats for one of said one or more rods, so that when the at least two jaws are closed and tightened on the frame, the one or more seats surround and tighten a portion of the rod, thereby preventing a relative movement of the rod with respect to an axis of the locking mechanism.

2. The device according to claim 1, wherein said one or more seats are arranged between two walls extending from one jaw.

3. The device according to claim 2, wherein said lever is pivoted to said jaw by means of two pins aligned with each other and inserted into holes made in the walls extending from this jaw and in two walls extending from the lever.

4. The device according to claim 3, wherein said walls extending from the lever comprise a cam surface.

5. The device according to claim 1, wherein said one or more seats have a concave shape suitable for receiving a portion of a sphere arranged at one end of a rod.

6. The device according to claim 1, wherein the seat of a jaw of said one or more seats is connected with the outside through an opening with a substantially frustoconical shape.

7. The device according to claim 1, wherein said one or more seats are so shaped that when the jaws are tightened on the frame the rod can rotate around one, two or three axes and/or translate along an axis with respect to the locking mechanism.

8. The device according to claim 1, wherein said one or more seats have a substantially cylindrical concave shape, wherein a seat of the first jaw of said one or more seats has externally a substantially frustoconical shape, which is provided with longitudinal slots and which is complementary to a cavity, also with a substantially frustoconical shape, of a seat of the second jaw of said one or more seats of the same locking mechanism, so that when these jaws are tightened on the frame, the seats are coupled, the seat of the first jaw is deformed and tightens a portion of the rod, thereby preventing a sliding of the rod with respect to the locking mechanism.

9. The device according to claim 1, wherein the cross-section of a portion of the frame is substantially elliptical.

10. The device according to claim 9, wherein the major axis of the ellipse of said cross-section is substantially parallel to a longitudinal axis (L) of the frame.

11. The device according to claim 1, wherein the cross-section of a portion of the frame has a substantially trapezoidal shape, with the major base arranged towards the center of the frame and the minor base towards the outside.

12. The device according to claim 1, wherein the frame is provided with one or more radial holes.

13. The device according to claim 1, wherein one or more circular or partially circular ribs and/or grooves are arranged along the frame.

14. The device according to claim 13, wherein the jaws of the locking mechanism comprises inner surfaces provided with ribs or grooves which carry out a form coupling with corresponding grooves or ribs arranged along the frame, so that the rod can be fixed to the frame by means of this locking mechanism with an orientation parallel to the central axis of the frame or inclined with respect to the latter with a given angle defined by the relative position of these ribs or grooves.

15. The device according to claim 1, wherein the frame comprises more frame portions connected to each other.

16. The device according to claim 15, wherein the portions of the frame are joined together by means of a screw inserted respectively in two holes that are formed at one end of these portions, are aligned with each other and are substantially parallel to the central axis (C) of the frame, in which the adjacent ends of the portions are shaped with complementary profiles so as to achieve a form coupling in the region where the screw passes through these holes.

17. The device according to claim 16, wherein said portions are joined by a screw screwed into a nut, in which the ends of the portions are arranged between the head of the screw, housed in a seat formed in a portion, and the nut, housed in a seat formed in the other portion.

18. The device according to claim 17, wherein around the hole for the screw the end of a portion of the frame is provided with a protrusion or recess which carries out a form coupling with a corresponding recess or protrusion formed in the contiguous end of the other portion of the frame.

19. The device according to claim 15, wherein an end of a portion of the frame is provided with a flexible hook suitable for being snapped into a corresponding cavity formed in one end of the adjacent portion of the frame.

20. The device according to claim 15, wherein an end of a portion of the frame is provided with a pin which is arranged along an axis substantially parallel to an axis tangent to the frame and is suitable for being inserted into a corresponding hole formed in one end of the adjacent portion of the frame.

21. The device according to claim 1, wherein the outer wall of the frame is provided with grooves or ribs substantially parallel to the central axis (C) of the frame.

22. The device according to claim 1, wherein the rod is provided with a clamp suitable to mechanically connect an elongated member to the frame.

23. The device according to claim 22, wherein said clamp is arranged at one end of the rod and comprises a movable part suitable to lock the elongated member so that it forms with the central axis the rod an angle comprised between 60° and 120°.

24. The device according to claim 1, wherein the rod is provided with a housing for a cable clamp, which housing is provided with a slot suitable to be crossed by a wire tightened by the cable clamp.

25. The device according to claim 1, wherein the locking mechanism is provided with a flexible hook suitable for engaging in a seat made in the lever.

26. The device according to claim 1, wherein said frame and/or rod and/or locking mechanism is made of a composite material, in particular containing carbon fibers, more in particular short carbon fibers.

* * * * *